ized application of amines to selectively reduce acrolein and furfural impurities.

United States Patent [19]

Bauer, Jr. et al.

[11] Patent Number: 5,571,386
[45] Date of Patent: Nov. 5, 1996

[54] PROCESS FOR GRADE ACRYLIC ACID

[75] Inventors: William Bauer, Jr., Huntingdon Valley, Pa.; Timothy A. Hale, Houston, Tex.; Robert M. Mason, Roslyn; Rita K. Upmacis, North Wales, both of Pa.

[73] Assignee: Rohm and Haas Company, Philadelphia, Pa.

[21] Appl. No.: 251,762

[22] Filed: May 31, 1994

[51] Int. Cl.⁶ .................................................. B01D 3/34
[52] U.S. Cl. ...................... 203/38; 203/71; 203/DIG. 21; 562/600
[58] Field of Search ................................. 203/59, 38, 14, 203/71, DIG. 21; 562/600

[56]  References Cited

U.S. PATENT DOCUMENTS

| | | | |
|---|---|---|---|
| 3,674,651 | 7/1972 | Otsuki et al. | 203/59 |
| 3,725,208 | 4/1973 | Maezawa et al. | 203/3 |
| 3,893,895 | 7/1975 | Dehnert et al. | 203/59 |
| 4,828,652 | 5/1989 | Schropp | 203/38 |
| 5,208,370 | 5/1993 | Bauer, Jr. et al. | 562/600 |

FOREIGN PATENT DOCUMENTS

| | | |
|---|---|---|
| 518214 | 1/1976 | Japan . |
| 312191 | 6/1988 | Japan . |
| 24459 | 4/1991 | Japan . |
| 1346737 | 2/1974 | United Kingdom . |

OTHER PUBLICATIONS

CA 81: 121364.
CA: 80: 96566.
CA 80: 70336.
European Search Report dated Sep. 29, 1995.
Research Disclosure 167066 dated Feb. 20, 1978.

*Primary Examiner*—Virginia Manoharan
*Attorney, Agent, or Firm*—Joseph F. Leightner; Richard A. Haggard

[57] ABSTRACT

The invention provides a continuous process for producing a pure grade of acrylic acid having residual aldehyde levels under 10 parts per million. The process applies two groups of amines sequentially and continuously in selectively reducing acrolein and furfural and may be advantageously conducted in the presence of maleic acid and maleic anhydride impurities.

8 Claims, No Drawings

PROCESS FOR GRADE ACRYLIC ACID

This invention relates to a process for purifying acrylic acid. More specfically, the process is a continuous process which provides a pure grade acrylic acid containing very low levels of residual aldehyde.

In the manufacture of acrylic acid by catalytic oxidation of propylene, acrylic acid ("AA") and oxidation byproducts initially are obtained in aqueous AA solution before further purification. In an "extraction/distillation procedure," the aqueous AA solution is extracted with a suitable organic solvent yielding an AA extract which then is azeotropically distilled and dehydrated, thus removing water from the extract and recovering the organic solvent for recycle. In another purifying procedure, a "direct distillation procedure," the aqueous solution extraction step is bypassed and the aeotropic distillation and dehydration applied directly to the aqueous AA solution. By either procedure, the resulting dehydrated AA, or "crude" AA, contains acid impurities, such as acetic acid, maleic acid and maleic anhydride, and also contains aldehyde impurities, such as acrolein, furfural, and benzaldehyde, and other oxidation byproducts. Acetic acid may be removed from the dehydrated AA by fractional distillation to give a low acetic acid AA, also designated "crude" AA, still containing the other components. In the extraction procedure, some of the maleic acid and other acid impurities are rejected to the waste water and thus contribute to expensive waste treatment. In the direct distillation procedure, these same impurities become a waste organic oil which can be burned for its fuel value. Thus, while both processes are practiced commercially, the direct distillation procedure is preferred for newer plants even though its use increases the difficulty in purifying AA containing appreciable levels of maleic acid and maleic anhydride. The present invention can be employed with both processes and is particularly advantageous for the direr distillation process.

Conventional fractional distillation of crude AA ("CAA") is capable of removing most of the maleic acid and maleic anhydride impurities and other high boiling impurities such as terephthalic acid, thus providing a distilled AA that is useful as starting material for producing acrylate esters or some polymers. However, conventional fractional distillation alone is not effective in reducing aldehydes to necessary levels for a pure grade acrylic acid ("PGAA") useful for producing polymers having average molecular weights higher than those of polymers obtained from distilled AA. To obtain PGAA, the CAA from either the extraction/distillation or direct distillation procedure must be purified beyond that achieved by conventional fractional distillation because residual impurities, particularly the aldehydes, interfere with polymerization reactions; aldehyde levels individually must be below about ten parts per million (ppm), more preferably below five ppm, and most preferably below one ppm. PGAA having these aldehyde levels is useful in producing, for example, superabsorbent polymers and polymers efficient as dispersants for oil well drilling muds and as flocculating agents.

It is known that aldehydes may be reduced to ppm levels in AA by distilling AA in the presence of amines or similar compounds. For example, U.S. Research Disclosure no. 167066 discloses that furfural is reduced to <1 ppm by treating crude or distilled acrylic acid with small amounts of phloroglucinol, ortho (o-) phenylenediamine, or aniline; these amines are believed to complex with or decompose furfural to give a product which then may be separated by fractional distillation. U.S. Pat. No. 3,725,208 ("'208") discloses that at least one of the following: sulfuric acid, hydrazine, phenylhydrazine, aniline, monoethanolamine, ethylene diamine, or glycine, when added batchwise to partially purified (presumably predistilled) "crude grade" acrylic acid containing aldehydes and the resulting mixture heated for 3 hours at 70° C. prior to fractional distillation, results in an AA distillate containing reduced levels of aldehydes. U.S. Pat. No. 4,828,652 ("'652") teaches that aminoguanidine or its salts are effective when used in ratios of 1 to 3 moles per mole of aldehyde and with at least 1–1.5 hour residence times before fractional distillation of a "technical grade" (again, presumably a distilled grade) of a crude grade AA.

There are problems, however, with the above mentioned aldehyde-reducing methods. For example, known methods utilize so-called single or one-shot amine addition to the crude grades of AA or to a distilled grade of a crude AA, and require appreciable residence time prior to distillation, as disclosed in the '652 patent. That patent also disclosed that previous efforts involving the addition of hydrazine or aqueous hydrazine solutions required an excess of about 4 moles of hydrazine per mole of aldehyde, and special distillation conditions, to achieve a furfural content under 5 ppm; furthermore, under those conditions, the distillation column became coated with byproducts. Although the '208 patent disclosed that amines such as aniline, monoethanolamine and ethylenediamine can be used, under the disclosed conditions the lowest residual aldehyde contents were obtained only with hydrazine or phenylhydrazine and high levels and long residence times were required to achieve low aldehyde level. Additional problems exist when maleic acid and maleic anhydride are present; when their combined level exceeds about 0.1 wt % in CAA, massive solids formation may occur with the excess amine used in either a batch or continuous method. These solids can foul equipment and cause downtime for cleaning. Additionally, because of the competitive reaction of amine with maleic anhydride, excessive quantities of amine need to be added because the reaction with maleic anhydride is kinetically favored over the reaction with furfural and benzaldehyde. Reaction with maleic anhydride may be avoided by predistilling the CAA, but this is a costly step which would beneficially be eliminated. It further has been found that another problem arises if amine is added only to the top or near the top of a fractional distillation column while distilling CAA; amine addition in this manner causes excessive polymer and other solids formation within the column when the CAA contains more than about 10 ppm of acrolein.

Thus, there is need of an efficient process, particularly a continuous process, to produce PGAA from CAA when the CAA contains not only aldehydes but also the typical impurities mentioned above, particularly maleic acid and maleic anhydride. We have discovered an economical, continuous process for reducing aldehydes in CAA containing substantial levels of acrolein, furfural, and maleic acid and anhydride. The process yields a PGAA having less than 10 ppm, and is capable of providing less than 1 ppm, of any individual residual aldehyde without requiring a predistillation of CAA to remove maleic anhydride. Features of the invention also are applicable to earlier processing steps associated with preliminary sources of AA, as will be shown. Further, the inventive process prevents fouling of equipment with polymer and other solids. The process also provides PGAA with levels of maleic anhydride below 100 ppm and advantageously provides for minimal use of expensive amines and minimal generation of new waste materials as compared to known processes.

Broadly described, the inventive process uses two selected groups of amines at different points of the continuous process in providing PGAA. In one embodiment, one or more amine from one selected group of amines (Group A) is added to CAA to provide a crude acrylic acid feed stream. Within the CAA feed stream, the Group A amine rapidly reacts with acrolein and other "light" aldehydes (aldehydes boiling lower than AA), effectively removing them from volatilizing in the column. The CAA feed stream is fed to a fractional distillation column and distilled. The fractionation power of the column retains maleic acid, maleic anhydride and higher boiling components, such as terephthalic acid, near the bottom of the column. Concurrently with the distillation of the CAA feed stream, an amine feed stream of one or more amine from another selected group of amines (Group B) is introduced at or near the top of the column to facilitate removal of any remaining residual volatile aldehydes, particularly furfural, and maleic anhydride. The resulting distillate, which may include polymerization stabilizers, is PGAA.

More specifically, there is provided a continuous process for producing a pure grade acrylic acid (PGAA) comprising the steps of:

a) feeding to a final distillation column a crude acrylic acid feed stream at a temperature of from 25° to 100° C., the feed stream comprising:
 i) a crude acrylic acid, and
 ii) a minimum effective level of from 0.1 to 2.0 molar ratio, based on total moles of aldehydes and maleic acid and maleic anhydride in the crude acrylic acid, of one or more of a Group A amine selected from the group consisting of:
  i) a primary arylamine of structure (I),

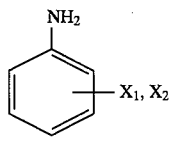

wherein $X_1$ and $X_2$ are selected from the group consisting of H, $NR_2$, OR, $C_1$, and R, wherein R is selected from H or $C_1$–$C_6$ alkyl;
  ii) a hydrazine, optionally its hydrate, of structure $R^2$—NH—$NH_2$, wherein $R^2$ is selected from H, phenyl, 4-nitrophenyl, or 2,4-dinitrophenyl;
  iii) an alkylenepolyamine of structure (II)

wherein $R_3$ is selected from H or a $C_1$–$C_6$ alkyleneamine, and $R^4$ is a $C_1$–$C_6$ alkyleneamine; and
  iv) an α-amino acid selected from the group consisting of structure III

wherein $R^5$ is selected from H, R, or $R^4$; arginine, aspartic acid, glutamic acid, histidine, and methionine;

b) concurrently feeding to an upper portion of the final distillation column an amine feed stream comprising a minimum effective level of from 0.01 to 1.0 molar ratio, based on total moles of aldehydes and maleic acid and maleic anhydride in the crude acrylic acid, of one or more of a Group B amine selected from the group consisting of o-, m-, p-phenylenediamine, 4-nitrophenylhydrazine, and 2,4-dinitrophenylhydrazine; and c) fractionally distilling the crude acrylic acid feed stream through the final distillation column, distilling off PGAA having a residual individual aldehyde content less than 10 ppm.

The continuous process also may be carried out by adding the amine from Group A to a preliminary column used in preparing CAA, e.g., the azeotropic distillation column or an acetic acid removal column. The resulting CAA is fed to the final distillation column while concurrently feeding amine from Group B to the upper portion of this final distillation column and distilling off PGAA.

As described previously, CAA is dehydrated AA and typically contains the following acids and aldehydes in the weight amounts indicated: for example, acrolein, ranging from several ppm to about 300 ppm; benzaldehyde and furfural, each about 200–400 ppm; maleic acid and maleic anhydride (combined) up to about 1.0 wt. % (and measured as maleic acid); and other components, such as acetic acid and terephthalic acid. Aqueous AA solutions and the AA extract are AA sources preceding CAA and contain the same acids and aldehydes as the CAA, and water.

In making up the CAA (or other AA source) feed stream, the Group A amine may be added to the CAA (or other AA source) either neat or as a solution in a suitable solvent such as water or a saturated carboxylic acid, such as propionic, hexanoic or valeric acid. The Group A amine is selected from the amines previously described, and as further defined here. The R-alkyl group of structure (I) of the primary arylamine is a $C_1$–$C_6$ alkyl, that is an alkyl group containing from 1 to 6 carbon atoms in any isomeric form, such as methyl, ethyl, propyl, isopropyl, n-, iso-, or sec-butyl, hexyl, and isomers thereof. Disubstituted primary arylamines, such as diaminotoluenes and dimethylanilines, are also effective. The hydrazines (or hydrates) of $R^2$—NH—$NH_2$ have been defined; the hydrate has the advantage of ease and safety in handling. The $C_1$–$C_6$ alkylene group, $R^3$ and $R^4$, of the alkylenepolyamine contains from 1 to 6 carbon atoms, such as methylenic, ethylenic, propylenic, butylenic, hexylenic, and isomers thereof, and bears a primary amine. Examples of structure II alkylenepolyamine include ethylenediamine, diethylenetriamine and dipropylenetriamine. The alpha-amino acid is as described.

The Group A amine is selected to react rapidly and substantially irreversibly with acrolein and other light aldehydes present in CAA or other AA sources preceding CAA. Most Group A amines react in-line as the CAA or other AA source are being led, with the amine, to a distillation column; provision also can be made to extend residence time by methods known in the art, such as by use of a buffer tank in the continuous feed line. While relatively expensive amines, such as the phenylenediamines, are included in group A, it is preferred to use less expensive amines such as aniline, o-methylaniline, hydrazine hydrate, diethylenetriamine, lysine, methionine, and glycine that are particularly effective with acrolein. (Alkyl amines, such as butyl amine, were found to have lower reaction rates and required higher use levels than, for example, aniline and other "faster-reacting" amines and, accordingly, are not included as Group A amines.) Generally, those Group A amines and their mixtures that are liquids at temperatures below 70 ° C. are easy to use. For reasons of cost, efficiency, availability, and ease of handling, those amines of Group A preferred for use in the invention include aniline, o-, m- and p-methylaniline, hydrazine and hydrazine hydrate, diethylenetriamine, glycine, lysine and methionine; more preferred, due to their cost and efficiency in reducing acrolein impurity, are aniline, o-methylaniline, hydrazine, hydrazine hydrate; aniline is most preferred.

At the same time that the CAA feed stream is fed to the final distillation column, one or more of an amine of Group B is fed, either neat or as a solution as described for the Group A amine addition, to an upper portion of the same column, that is, is fed to the top or within the upper 30% of the column, and always above the CAA feed stream. Effective Group B amines are stated above and are selected to react rapidly and essentially irreversibly with furfural. Preferred Group B amines, due to their cost, availability and efficiency include meta-phenylenediamine, 4-nitrophenylhydrazine and 2,4-dinitrophenylhydrazine; of these, meta-phenylenediamine is most preferred. PGAA having residual individual aldehyde level less than 5 ppm is readily achieved using the preferred amines and less than 1 ppm using the most preferred amines.

Another embodiment of the invention utilizing the same amine groups in similar manner is the addition of one or more amine of Group A to an AA source, for example, to an aqueous AA solution, to form an AA source feed stream which is fed to an azeotropic dehydration column. After dehydration, the resulting CAA has a low acrolein content (<10 ppm) and is dry. The AA source also can be an extract, that is, an aqueous AA solution which has been extracted with a suitable organic solvent; the resulting AA extract is fed to the azeotropic dehydration column in place of the aqueous acrylic acid solution. It is also possible to feed the Group A amine to the azeo tropic dehydration column as a separate stream as either AA source is fed to the column. The resulting low acrolein CAA (as now dehydrated) is then fed, optionally, to another fractional distillation column for acetic acid removal, thus yielding a low acrolein CAA having a low (<2,000 ppm) acetic acid content, or directly to a final distillation column, i.e., a high purity acrylic acid distillation column, where steps b) and c) as described above, are carried out. An advantage of adding the Group A amine to an aqueous AA solution or extract is that either solution does not contain maleic acid in its anhydride form, thus not wasting the Group A amine by its reaction with maleic anhydride.

Thus, there is also provided a continuous process for producing a pure grade acrylic acid (PGAA) comprising the steps of:

a) feeding to a first distillation column an acrylic acid source feed stream at a temperature of from 25° to 100° C., the source feed stream comprising i) an acrylic acid source selected from the group consisting of an aqueous acrylic acid solution and an acrylic acid extract; ii) a minimum effective level of from 0.1 to 2.0 molar ratio, based on total moles of aldehydes and maleic acid and maleic anhydride in the acrylic acid source, of one or more of a Group A amine selected from the same group A amines described in the preceding a) ii section;
b) dehydrating the acrylic acid source feed stream to provide a low acrolein crude acrylic acid having an acrolein content less than 10 ppm; c) optionally distilling off acetic acid from-the low acrolein crude acrylic acid to provide a low acrolein crude acrylic acid having a reduced acetic acid level; d) subsequently feeding to a final distillation column i. the low acrolein crude acrylic acid, and ii. concurrently, to an upper portion of the final distillation column, an amine feed stream comprising a minimum effective level of from 0.01 to 1.0 molar ratio, based on total moles of aldehydes and maleic acid and maleic anhydride in the low acrolein crude acrylic acid, of one or more of a Group B amine selected from the group consisting of o-, m-, p-phenylenediamine, 4-nitro-phenylhydrazine, and 2,4-dinitrophenylhydrazine; and e) fractionally distilling the low acrolein crude acrylic acid through the final distillation column, distilling off PGAA having a residual individual aldehyde content less than 10 ppm.

Another embodiment of the invention utilizing the same amine groups in similar manner is the addition of one or more amine of Group A to a CAA having a high (>2,000 ppm) level of acetic acid. This high acetic acid-containing CAA feed stream may be fed to an acetic acid distillation column, that is, a distillation column used for effectively reducing, by its distillation, acetic acid from the CAA. Distillation of the Group A-treated CAA yields a low acrolein (also now low acetic acid) CAA. (The Group A amine can be fed to the acetic acid removal column as a separate stream as the high acetic acid CAA is fed to the column.) Subsequently, the low acrolein CAA is fed to a final distillation column, i.e., a high purity acrylic acid distillation column, where the final distillation steps, previously described, are carried out.

Thus, there is additionally provided a continuous process for producing a pure grade acrylic acid (PGAA) comprising the steps of a) feeding to an acetic acid distillation column a feed stream at a temperature of from 25° to 100° C., the feed stream comprising i) a high acetic acid-containing crude acrylic acid; and ii) a minimum effective level of from 0.1 to 2.0 molar ratio, based on total moles of aldehydes and maleic acid and maleic anhydride in the high acetic acid-containing crude acrylic acid, of one or more of a Group A amine selected from the same group A amines described in the preceding a) ii section; b) distilling off acetic acid from the feed stream to provide a low acrolein, crude acrylic acid having an acetic acid content less than 2,000 ppm and an acrolein content <10 ppm; c) subsequently feeding to a final distillation column i. the low acrolein crude acrylic acid, and ii. concurrently, to an upper portion of the final distillation column, an amine feed stream comprising a minimum effective level of from 0.01 to 1.0 molar ratio, based on total moles of aldehydes and maleic acid and maleic anhydride in the low acrolein crude acrylic acid, of one or more of a Group B amine selected from the group consisting of o-, m-, p-phenylenediamine, 4-nitrophenylhydrazine, and 2,4-dinitrophenylhydrazine; and d) fractionally distilling the low acrolein crude acrylic acid through the final distillation column, distilling off PGAA having a residual individual aldehyde content less than 10 ppm.

An advantage of these approaches using, for example, either aqueous sources of AA or high acetic acid-containing CAA, is that acrolein and other light aldehydes are removed early in the AA purification process, with the added benefit of reducing the tendency for the AA to polymerize while being purified, thus allowing a reduction in polymerization inhibitor level during further processing. Thus, Group A can be used effectively in partially purifying acrylic acid in a continuous process step prior to feeding to the final fractional distillation column yielding PGAA and avoiding some of the tendency of acrylic acid to polymerize while being purified.

The same preferred Group A and Group B amines used in the first embodiment described above are preferred in the aqueous solution sourced AA and high acetic acid CAA embodiments of the invention. PGAA having <10 ppm residual individual aldehyde, preferably <5 ppm, most preferably <1 ppm, may be obtained from the processes described, the preferred amines readily achieving <5 ppm and the more preferred achieving <1 ppm.

Any distillation of the invention is carried out under reduced pressure, typically less than 200 mm Hg, with a column bottom temperature maintained below 150° C., preferably less than about 100° C., to minimize the loss of AA as polymer. When the Group A amine is added to the CAA or other AA sources as described, the temperature of the AA-containing feed stream should be greater than 25° C. and preferably greater than 40° C., up to a temperature of 100° C.; a temperature range from 40° to 80° C. is preferred. At these temperatures, fewer solids are generated than at temperatures of 25° C. and below.

The continuous processes of the invention are distinguished from "batch" processes; in the latter, a fixed quantity of CAA or an AA source is charged to a distillation unit, reacted with a fixed amount of amine to reduce aldehyde content (via a single or on&shot amine addition) and subsequently distilled to provide a fixed quantity of purified product. Batch processes, due to the time required for charging, reaction, distillation, and cleanout, characteristically are of lower productivity than the continuous processes of the invention. The inventive continuous processes also are distinguished from "combined batch and continuous" processes where, in the latter, the treatment of CAA or an AA source with an amine to reduce aldehyde content is carried out first in a batch reactor then the pretreated CAA or other source is fed continuously to a distillation column. The latter processes require additional reactors and storage vessels which are unnecessary with the continuous process of this invention.

The "minimum effective level" of the one or more Group A amine added to the feed of a distillation column (or directly to the column itself) is determined by measuring the acrolein content of the output (e.g. a distillate) resulting from the distillation column or other unit to which the Group A amine-treated stream is fed. (In the embodiments where the Group A amine is added at points in the process prior to the final distillation step, the acrolein content is measured in the major AA-containing stream produced by the unit, e.g. a bottom stream, into which the Group A-treated stream is fed.) In any case, the Group A amine is added to the unit's feed source until the measured acrolein level is below 10 ppm. The level of Group A amine required to reduce the acrolein level to <10 ppm is defined as the "minimum effective level" for the Group A amine(s). Group A amine minimum effective levels higher than the minimum effective level usually are needed to achieve lower levels of residual acrolein, such as 5 and 1 ppm, but all Group A amine use levels are within the range specified previously.

The minimum effective level of the Group B amine, which in all embodiments is added to the upper portion of the final distillation column, is determined by measuring the furfural content of the distillate of the final distillation column. Then, increasing levels of the Group B amine are added to the final distillation column until the measured furfural level is <10 ppm. The level of Group B amine required to just reduce the furfural level to <10 ppm is defined as the "minimum effective level" for the Group B amine(s). In any of the inventive embodiments, the Group B minimum effective level is determined after the minimum effective level for the Group A amine is determined and as Group A amine continues to be fed. Group B amine minimum effective levels higher than the minimum effective level usually are needed to achieve lower levels of residual furfural, such as 5 and 1 ppm, but all Group B amine use levels are within the range specified previously. The resulting PGAA from all embodiments of the invention have residual individual aldehyde contents below 10 ppm.

EXAMPLES

General

In the Examples and Comparative Examples these abbreviations are used: CAA, crude acrylic acid; HQ, hydroquinone; MeHQ, monomethyl ether of hydroquinone; mPD, m-phenylenediamine; PTZ, phenothiazine. For compositional analysis, gas chromatography was used for acrolein, benzaldehyde, and furfural and high performance liquid chromatography for maleic acid and anhydride, both methods sensitive to <1 ppm. The maleic acid and anhydride analytical results were combined because the analytical method converted any anhydride into the acid; thus, results for maleic acid and anhydride are reported as "maleic acid/anhydride." (When maleic acid/anhydride is reported for the distillate, it is most likely present as maleic anhydride because it is known from vapor pressure data that negligible maleic acid distills overhead in a column where acrylic acid is distilled overhead.) Where amines were added to CAA or other AA sources, the amount added was expressed as a molar ratio of the amine to the total moles of acrolein, benzaldehyde, furfural, and maleic acid/anhydride measured in the feed stream of the unit to which the feed stream is added. In the case of the distillation examples, the distillate analyses typically were the average of two or more analyses of hourly samples taken during steady operation. Analyses above 100 ppm were rounded off to two significant figures.

Screening tests were conducted by adding indicated levels of amine to aliquots of a stock solution of PGAA which had been spiked with the following impurities at the ppm levels indicated in the Examples: acrolein, benzaldehyde, furfural and maleic anhydride. (In Tables I–V, acrolein, benzaldehyde, furfural and maleic acid/anhydride are denoted by the symbols A, B, F and M, respectively, and results are in ppm.) The aliquots containing the amine were stirred for thirty minutes at 23°–25° C. and then immediately analyzed. After about five days at 23°–25° C., the aliquots containing amine were reanalyzed. Control samples are those spiked samples into which no amine was added.

The following criteria for the screening tests were used to estimate which amines would be useful as either Group A or Group B amines in the invention. An amine was judged to be a useful Group A amine if it reduced acrolein to <10 ppm at a molar ratio of amine of up to 2. The amine was judged particularly effective if acrolein reduction occurred within 30 minutes. For an amine to be useful as a Group A amine, it did not need to reduce the levels of benzaldehyde and/or furfural. An amine was judged to be a useful Group B amine if it (i) showed a >50% reduction within 30 minutes in the level of furfural at a molar ratio of amine of less than 1.0, and (ii) showed a reversibility of reaction with furfural (at an amine molar ratio of less than 1.0) which generated, after about 5 days, less than 70% of the initial level of furfural in the control sample.

Example 1

Preparation of PGAA where Group A Amine is Aniline and Group B Amine is mPD

A one-inch, fifteen tray Oldershaw column fitted with a steam heated reboiler was used. The CAA, containing 85 ppm acrolein, 220 ppm benzaldehyde, 240 ppm furfural, and 7200 ppm maleic acid/anhydride, was preheated by passing it through a heat exchanger. Aniline was added (0.5 molar ratio) to the flowing preheated CAA and the flowing CAA feed stream was maintained at the desired temperature during feeding to the "pot," i.e., the vessel at the bottom of the column. The operating conditions for the column were: overhead pressure, about 35 mm Hg; CAA rate, about 211 gram/hour; reflux ratio, about 1.6; percent of total feed removed as distillate, about 86%; CAA feed stream temperature, about 50° C.; pot temperature, about 83° C.; and overhead temperature, about 65° C. For polymerization inhibition, the following inhibitor levels were fed based on the CAA rate: about 0.5 wt % air to the reboiler, about 0.1 wt % MeHQ to the condenser, about 0.03 wt % PTZ and about 0.06 wt % HQ to tray 11 (numbered bottom to top). Concurrently, mPD was added (0.08 molar ratio) at tray fifteen, the top of the column. At steady conditions over a period of seven hours, the distillate of PGAA consistently contained <1 ppm each of acrolein, benzaldehyde, and furfural, and 2 ppm of maleic acid/anhydride. There were neither problems with solids formation in the feed lines to the pot or in the pot, nor were there any polymer or other solids problems in the column.

Example 2

Preparation of PGAA where Group A Amine is Hydrazine Hydrate and Group B Amine is mPD The conditions of Example 1 were repeated except that (i) hydrazine hydrate was fed to the pot (0.5 molar ratio) instead of aniline, (ii) mPD (0.2 molar ratio) was fed to tray eleven, and (iii) the CAA contained 91 ppm acrolein, 210 ppm benzaldehyde, 250 ppm furfural, and 6100 ppm maleic acid/anhydride. At steady conditions over a period of two hours, the distillate of PGAA consistently contained <1 ppm each of acrolein, benzaldehyde, and furfural, and 2 ppm of maleic acid/anhydride. There were neither problems with solids formation in the pot nor were there any polymer or other solids problems in the column. Some minor solids were observed in the CAA feed stream line, but at a level which did not interfere with continuous operation.

Comparative Example 1

CAA Distillation without Group A or B Amine Addition

Comparative Example 1 employed conditions similar to those described in Example 1, except that (i) no Group A amine was fed to the pot, (ii) no Group B amine was fed to the column, and (iii) the CAA contained 66 ppm acrolein, 230 ppm benzaldehyde, 270 ppm furfural, and 6600 ppm maleic acid/anhydride. At steady conditions over a period of eighteen hours, the distillate consistently contained 38 ppm acrolein, 3 ppm benzaldehyde, 91 ppm furfural, and 70 ppm of maleic acid/anhydride. There were neither problems with solids formation in the feed lines to the pot or in the pot, nor were there any polymer or other solids problems in the column, but without any amine addition, the levels of impurities in the distillate far exceed those required for PGAA.

Comparative Example 2

CAA Distillation where Group A Amine is Aniline and with No Group B Amine Addition Comparative Example 2 employed conditions similar to those described in Example 1, except that (i) aniline was fed to the pot (0.6 molar ratio), and (ii) no Group B amine was fed to the column. At steady conditions over a period of two hours, the distillate consistently contained <1 ppm acrolein, 1 ppm benzaldehyde, 46 ppm furfural, and 58 ppm of maleic acid/anhydride. There were neither problems with solids formation in the feed lines to the pot or in the pot, nor were there any polymer or other solids problems in the column. Thus, although aniline fed to the pot sufficiently reduced acrolein, it did not sufficiently reduce furfural to provide a satisfactory PGAA.

Comparative Example 3

CAA Distillation where Group A Amine is Aniline and CAA Feed Stream is at 23°–25° C.

Comparative Example 3 employed conditions similar to those described in Example 1, except that (i) aniline was fed to the pot (0.6 molar ratio), (ii) no Group B amine was fed to the column, (iii) the CAA contained 91 ppm acrolein, 210 ppm benzaldehyde, 250 ppm furfural, and 6100 ppm maleic acid/anhydride, and (iv) the CAA feed stream to the column was maintained at 23°–25° C. Under these conditions, the CAA feed line was plugged with solids after 4 hrs, forcing column shutdown. The solids were identified by 1H NMR spectroscopy as N-phenylmaleamic acid, the reaction product of aniline and maleic anhydride.

Comparative Example 4

CAA Distillation Without Group A Amine and where Group B Amine is mPD

Comparative Example 4 employed conditions similar to those described in Example 1, except that (i) no Group A amine was fed to the pot, (ii) mPD was fed to the column (0.05 molar ratio), (iii) the CAA contained 69 ppm acrolein, 230 ppm benzaldehyde, 270 ppm furfural, and 8100 ppm maleic acid/anhydride, and (iv) the CAA feed stream to the column was maintained at 23°–25° C. At these conditions, the column suffered from heavy polymer and other solids formation and after 30 minutes was forced to shut down. Also, the distillate, just prior to shut down, contained 63 ppm acrolein, <1 ppm benzaldehyde, 4 ppm furfural, and 2 ppm maleic acid/anhydride. Thus, feeding amine to the upper portion of the column alone was not satisfactory for PGAA production because of polymer and other solids formation in the column preventing continuous operation. The data showed that heavy polymer and other solids formation occured in the column when no Group A amine was fed to the CAA but a Group B amine was fed to the upper portion of the column.

Comparative Example 5

Screening Tests Adding Primary Alkylamine to PGAA Spiked with Impurities

In Comparative Example 5, the general procedure described previously for screening tests was employed, except that the amines employed were primary alkylamines. The results are given in Table I in which the data show that representative primary alkylamines, n-butylamine and tert-octylamine, were not useful Group A (or Group B) amines. While primary alkylamines may have some utility in reducing acrolein, they would not be effective in producing PGAA.

TABLE I

Screening Tests Showing the Effect of Primary Alkylamines on Aldehyde Removal in Spiked PGAA

| Additive | Amine Molar Ratio | After Thirty Minutes | | | | After About Five Days | | | |
|---|---|---|---|---|---|---|---|---|---|
| | | A | B | F | M | A | B | F | M |
| Control - PGAA Spiked | 0 | 170 | 320 | 300 | 320 | — | — | — | — |
| n-Butylamine | 0.46 | 110 | 320 | 290 | 280 | 54 | 310 | 290 | 290 |
| n-Butylamine | 2.1 | 79 | 300 | 280 | 260 | 23 | 300 | 280 | 250 |
| Control - PGAA Spiked | 0 | 210 | 290 | 260 | 370 | — | — | — | — |
| Tert-octylamine | 0.47 | 190 | 280 | 270 | 360 | 110 | 270 | 240 | 340 |
| Tert-octylamine | 0.93 | 200 | 280 | 240 | 350 | 87 | 250 | 240 | 340 |

Example 3

Screening Tests Adding Primary Arylamine to PGAA Spiked with Impurities, to CAA, and to Aqueous Acrylic Acid Solution In Example 3, the general procedure described previously for screening tests was employed, except that (i) the amines employed were primary arylamines and (ii) the amine was added to aliquots of either stock PGAA spiked with impurities, or to CAA, or to aqueous acrylic acid solution. These sources of AA were used containing the ppm levels of acrolein, benzaldehyde, furfural and maleic acid/anhydride indicated in Table II. The aqueous acrylic acid solution contained about 35% water.

Based on the previously described criteria, Table II screening test data show that the following primary arylamines were effective as Group A amines: aniline, m-phenylenediamine, p-phenylenediamine, 1,5-diaminonaphthalene, p-aminophenol, p-methoxyaniline, p-chloroaniline, o-methylaniline, m-methylaniline, p-methylaniline and p-nitroaniline. In addition, Table II shows that m-phenylenediamine is an outstanding Group B amine; p-phenylenediamine also was a useful Group B amine.

TABLE II

Screening Tests Showing the Effect of Primary Arylamines on Aldehyde Removal in Spiked PGAA, CAA or Aqueous Acrylic Acid Solution

| Additive | Amine Molar Ratio | After Thiry Minutes | | | | After About Five Days | | | |
|---|---|---|---|---|---|---|---|---|---|
| | | A | B | F | M | A | B | F | M |
| Control - PGAA Spiked | 0 | 200 | 300 | 350 | 310 | — | — | — | — |
| p-Aminophenol | 0.12 | 69 | 300 | 370 | 200 | 30 | 320 | 400 | 310 |
| p-Aminophenol | 0.46 | 1 | 290 | 330 | 30 | <1 | 290 | 360 | 290 |
| p-Aminophenol | 0.89 | <1 | 270 | 220 | 6 | <1 | 290 | 370 | 280 |
| Control - PGAA Spiked | 0 | 130 | 210 | 170 | 190 | — | — | — | — |
| Aniline | 0.22 | 14 | 190 | 170 | 87 | <1 | 180 | 160 | 190 |
| Aniline | 0.46 | <1 | 150 | 120 | 25 | <1 | 170 | 150 | 210 |
| Aniline | 0.68 | <1 | 140 | 91 | 20 | <1 | 180 | 150 | 210 |
| Aniline | 0.93 | <1 | 120 | 79 | 32 | <1 | 160 | 140 | 200 |
| Aniline | 1.8 | <1 | 88 | 50 | 36 | <1 | 200 | 160 | 200 |
| Control - CAA | 0 | 150 | 250 | 260 | 7400 | — | — | — | — |
| Aniline | 0.32 | 8 | 260 | 270 | 4900 | — | — | — | — |
| Aniline | 0.50 | <1 | 230 | 220 | 3900 | — | — | — | — |
| Aniline | 1.0 | <1 | 90 | 20 | 3400 | — | — | — | — |
| Control - Aqueous AA | 0 | 40 | 130 | 110 | 4700 | — | — | — | — |
| Aniline | 0.23 | 19 | 140 | 120 | 4700 | 4 | 120 | 110 | 5000 |
| Aniline | 0.46 | 3 | 120 | 94 | 4600 | <1 | 100 | 86 | 5000 |
| Control - PGAA Spiked | 0 | 210 | 290 | 370 | 300 | — | — | — | — |
| p-Chloroaniline | 0.12 | 62 | 300 | 370 | 210 | 28 | 300 | 380 | 310 |
| p-Chloroaniline | 0.47 | <1 | 280 | 320 | 59 | <1 | 290 | 350 | 270 |
| p-Chloroaniline | 0.99 | <1 | 220 | 170 | 35 | <1 | 290 | 310 | 270 |
| Control - PGAA Spiked | 0 | 220 | 270 | 330 | 310 | — | — | — | — |
| 1,5-Diaminonaphthalene | 0.12 | 35 | 250 | 310 | 230 | 10 | 260 | 310 | 280 |
| 1,5-Diaminonaphthalene | 0.47 | <1 | 170 | 140 | 120 | <1 | 270 | 310 | 140 |
| 1,5-Diaminonaphthalene | 0.92 | <1 | 200 | 160 | 120 | <1 | 270 | 300 | 120 |
| Control - PGAA Spiked | 0 | 210 | 290 | 370 | 300 | — | — | — | — |
| p-Methoxyaniline | 0.13 | 71 | 300 | 380 | 200 | 32 | 300 | 370 | 310 |
| p-Methoxyaniline | 0.44 | <1 | 290 | 340 | 66 | <1 | 290 | 370 | 300 |
| p-Methoxyaniline | 0.93 | <1 | 270 | 230 | 42 | <1 | 300 | 370 | 300 |
| Control - PGAA Spiked | 0 | 190 | 380 | 430 | 300 | — | — | — | — |
| o-Methylaniline | 0.49 | 5 | 350 | 380 | 240 | <1 | 340 | 370 | 290 |
| o-Methylaniline | 0.99 | <1 | 300 | 290 | 170 | <1 | 320 | 350 | 240 |
| Control - PGAA Spiked | 0 | 200 | 340 | 280 | 380 | — | — | — | — |
| m-Methylaniline | 0.10 | 59 | 340 | 280 | 270 | 30 | 300 | 250 | 370 |
| m-Methylaniline | 0.44 | <1 | 310 | 250 | 140 | <1 | 320 | 260 | 350 |
| m-Methylaniline | 0.91 | <1 | 250 | 170 | 130 | <1 | 300 | 220 | 370 |

TABLE II-continued

Screening Tests Showing the Effect of Primary Arylamines on Aldehyde Removal in Spiked PGAA, CAA or Aqueous Acrylic Acid Solution

| Additive | Amine Molar Ratio | After Thirty Minutes | | | | After About Five Days | | | |
|---|---|---|---|---|---|---|---|---|---|
| | | A | B | F | M | A | B | F | M |
| Control - PGAA Spiked | 0 | 97 | 310 | 280 | 340 | — | — | — | — |
| p-Methylaniline | 0.13 | 28 | 300 | 270 | 310 | 38 | 320 | 300 | 330 |
| p-Methylaniline | 0.62 | <1 | 280 | 220 | 280 | <1 | 300 | 270 | 320 |
| p-Methylaniline | 1.0 | <1 | 260 | 180 | 300 | <1 | 310 | 280 | 370 |
| Control - PGAA Spiked | 0 | 130 | 300 | 300 | 310 | — | — | — | — |
| p-Nitroaniline | 0.14 | 36 | 270 | 280 | 270 | 7 | 270 | 270 | 300 |
| p-Nitroaniline | 0.54 | 4 | 260 | 270 | 110 | <1 | 280 | 250 | 160 |
| p-Nitroaniline | 1.1 | 4 | 250 | 260 | 62 | <1 | 270 | 260 | 180 |
| Control - PGAA Spiked | 0 | 100 | 190 | 170 | 220 | — | — | — | — |
| m-phenylenediamine | 0.12 | 12 | 190 | 170 | 140 | 3 | 180 | 190 | 210 |
| m-phenylenediamine | 0.25 | <1 | 170 | 150 | 48 | <1 | 170 | 160 | 170 |
| m-phenylenediamine | 1.0 | <1 | 72 | 22 | 13 | <1 | 33 | 5 | 120 |
| Control - CAA | 0 | 79 | 210 | 210 | 7800 | — | — | — | — |
| m-phenylenediamine | 0.13 | 2 | 200 | 170 | 6100 | — | — | — | — |
| m-phenylenediamine | 0.33 | <1 | 160 | 63 | 3700 | — | — | — | — |
| m-phenylenediamine | 0.67 | <1 | 1 | <1 | 3100 | — | — | — | — |
| Control - PGAA Spiked | 0 | 240 | 390 | 320 | 360 | — | — | — | — |
| p-phenylenediamine | 0.10 | 73 | 370 | 330 | 250 | 22 | 400 | 380 | 240 |
| p-phenylenediamine | 0.41 | <1 | 320 | 190 | 28 | <1 | 330 | 250 | — |
| p-phenylenediamine | 0.81 | <1 | 250 | 90 | — | <1 | 310 | 220 | 260 |
| p-phenylenediamine | 1.6 | <1 | 160 | 35 | — | <1 | 300 | 170 | 280 |

Example 4

Screening Tests Exploring the Effect of Temperature on Aniline Addition to PGAA Spiked with Impurities (23°–25° C. and 60° C.)

In Example 4, the general procedure described previously for the screening tests was employed, except that (i) the amine employed was aniline, (ii) the test was conducted at either 23°–25° C. or 60° C., and (ii) the aliquots containing the amine were analyzed only once, after 30 min. The results are given in Table III, the data showing that the rate of reaction of the components with aniline after thirty minutes, in descending order was: acrolein>maleic anhydride > furfural>benzaldehyde. This reactivity trend is the same for 23°–25° C. and for 60° C. However, at 60° C., benzaldehyde, furfural, and maleic anhydride levels are higher than at 23°–25° C. with the same level of aniline. Thus, also to the advantage of less solids (previously discussed), higher temperatures, such as 50°–60° C., are preferred when adding Group A amine to CAA or an AA source.

TABLE III

Screening Tests Showing the Effect of Temperature on Removal of Aldehydes by Aniline in Spiked PGAA

| Additive | Amine Molar Ratio | A | B | F | M |
|---|---|---|---|---|---|
| 23–25° C. | | | | | |
| Control - Spiked PGAA | 0 | 130 | 210 | 170 | 190 |
| Aniline | 0.22 | 14 | 190 | 170 | 87 |
| Aniline | 0.46 | <1 | 150 | 120 | 25 |
| Aniline | 0.68 | <1 | 140 | 91 | 20 |
| Aniline | 0.93 | <1 | 120 | 79 | 32 |
| Aniline 60° C. | 1.8 | <1 | 88 | 50 | 36 |
| Control - Spiked PGAA | 0 | 170 | 190 | 240 | 210 |
| Aniline | 0.38 | <1 | 190 | 230 | 130 |
| Aniline | 0.46 | <1 | 180 | 210 | 110 |
| Aniline | 0.68 | <1 | 180 | 200 | 120 |
| Aniline | 0.92 | <1 | 180 | 180 | 80 |

Example 5

Screening Tests Adding Hydrazine Hydrate and 2,4-Dinitrophenylhydrazine to PGAA Spiked with Impurities In Example 5, the general procedure described previously for the screening tests was employed, except that the amines employed were hydrazine and its derivatives. The results given in Table IV show that both hydrazine hydrate and 2,4-dinitrophenylhydrazine were effective as Group A amines; the latter amine was an outstanding Group B amine.

TABLE IV

Effect of Hydrazine Derivatives on Aldehyde Removal in Spiked PGAA

| Additive | Amine Molar Ratio | After Thirty Minutes | | | | After About Five Days | | | |
|---|---|---|---|---|---|---|---|---|---|
| | | A | B | F | M | A | B | F | M |
| Control - PGAA Spiked | 0 | 210 | 320 | 310 | 320 | — | — | — | — |
| Hydrazine Hydrate (55%) | 0.54 | 11 | 300 | 280 | 90 | <1 | 340 | 360 | 250 |
| Hydrazine Hydrate (55%) | 1.1 | <1 | 260 | 220 | 27 | <1 | 330 | 330 | 260 |
| Control - PGAA Spiked | 0 | 210 | 290 | 260 | 370 | — | — | — | — |
| 2,4-Dinitrophenylhydrazine | 0.11 | 110 | 250 | 220 | 350 | 100 | 250 | 230 | 170 |
| 2,4-Dinitrophenylhydrazine | 0.48 | <1 | 58 | 78 | 280 | 1 | 35 | 55 | 160 |
| 2,4-Dinitrophenylhydrazine | 0.96 | <1 | 2 | <1 | 64 | <1 | 2 | <1 | 53 |

Example 6

Screening Tests Adding Alkylenepolyamine or α-Amino Acid to PGAA Spiked with Impurities In Example 6, the general procedure described previously for the screening tests was employed, except that the amines employed were either alkylenepolyamines or α-amino acids. Here, glycine was added in aqueous solution. The results are given in Table V.

Table V screening test data show that diethylenetriamine, glycine, lysine, arginine and histidine were effective as Group A amines.

TABLE V

Effect of Alkylene Polyamines and α-Amino Acids on Aldehyde Removal in Spiked PGAA

| Additive | Amine Molar Ratio | After Thirty Minutes | | | | After About Five Days | | | |
|---|---|---|---|---|---|---|---|---|---|
| | | A | B | F | M | A | B | F | M |
| Alkylene Polyamines | | | | | | | | | |
| Control - PGAA Spiked | 0 | 210 | 290 | 250 | 300 | — | — | — | — |
| Diethylenetriamine | 0.12 | 76 | 290 | 240 | 280 | 40 | 300 | 240 | 190 |
| Diethylenetriamine | 0.51 | 30 | 280 | 220 | 190 | <1 | 300 | 220 | 62 |
| α-Amino Acids | | | | | | | | | |
| Control - PGAA Spiked | 0 | 210 | 290 | 250 | 300 | — | — | — | — |
| Glycine (in H$_2$O) | 0.37 | 92 | 300 | 250 | 220 | 25 | 280 | 200 | 270 |
| Glycine (in H$_2$O) | 0.74 | 88 | 300 | 250 | 200 | 3 | 240 | 160 | 250 |
| Control - PGAA Spiked | 0 | 200 | 290 | 360 | 310 | — | — | — | — |
| DL-Lysine | 0.12 | 120 | 280 | 330 | 310 | 22 | 250 | 280 | 250 |
| DL-Lysine | 0.44 | 47 | 270 | 330 | 290 | <1 | 240 | 130 | 200 |
| DL-Lysine | 0.87 | 39 | 270 | 300 | 280 | <1 | 180 | 10 | 160 |
| Control - PGAA Spiked | 0 | 240 | 270 | 330 | 320 | — | — | — | — |
| Arginine | 0.46 | 87 | 280 | 330 | 250 | <1 | 240 | 160 | 230 |
| Histidine | 0.45 | 62 | 260 | 310 | 320 | <1 | 260 | 210 | 310 |

We claim:

1. A continuous process for producing a pure grade acrylic acid (PGAA) comprising the steps of:

a) feeding to a first distillation column an acrylic acid source feed stream at a temperature of from 25° to 100° C., the source feed stream comprising:

i) an acrylic acid source selected from the group consisting of an aqueous acrylic acid solution and an acrylic acid extract, the acrylic acid source optionally containing acetic acid;

ii) a minimum effective level of from 0.1 to 2.0 molar ratio, based on total moles of aldehydes and maleic acid and maleic anhydride in the acrylic acid source, of at least one of a Group A amine selected from the group consisting of:

i) a primary arylamine of structure (I),

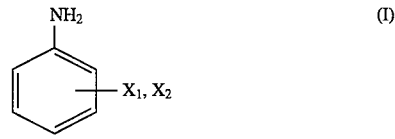

wherein $X_1$ and $X_2$ are selected from the group consisting of H, $NR_2$, OR, Cl, and R, wherein R is selected from H or $C_1$–$C_6$ alkyl;

ii) a hydrazine, optionally its hydrate, of structure $R^2$—NH—NH$_2$, wherein $R^2$ is selected from H, phenyl, 4-nitrophenyl, or 2,4-dinitrophenyl;

iii) an alkylenepolyamine of structure (II)

wherein $R^3$ is selected from H or a $C_1$–$C_6$ alkyleneamine, and $R^4$ is a $C_1$–$C_6$ alkyleneamine; and iv) an α-amino acid selected from the group consisting of structure III

wherein $R^5$ is selected from H, R, or $R^4$; arginine, aspartic acid, glutamic acid, histidine, and methionine;

b) dehydrating the acrylic acid source feed stream to provide a low acrolein crude acrylic acid having an acrolein content less than 10 ppm;

c) optionally distilling off acetic acid from the low acrolein crude acrylic acid to provide a low acrolein crude acrylic acid having a reduced acetic acid level;

d) subsequently feeding to a final distillation column
   i. the low acrolein crude acrylic acid having acrolein content less than 10 ppm, and
   ii. concurrently, to an upper portion of the final distillation column above the low acrolein crude acrylic acid feed, an amine feed stream comprising a minimum effective level of from 0.01 to 1.0 molar ratio, based on total moles of aldehydes and maleic acid and maleic anhydride in the low acrolein crude acrylic acid, of at least one of a Group B amine selected from the group consisting of o-, m-, p-phenylenediamine, 4-nitrophenylhydrazine, and 2,4-dinitrophenylhydrazine; and e) fractionally distilling the low acrolein crude acrylic acid through the final distillation column, distilling off PGAA having a residual individual aldehyde content less than 10 ppm.

2. The process of claim 1 wherein the Group A amine is selected from the group consisting of aniline, o-, m-, p-methylaniline, hydrazine, hydrazine hydrate, diethylenetriamine, glycine, lysine, and methionine, and the Group B amine is selected from the group consisting of m-phenylenediamine, 4-nitrophenylhydrazine and 2,4-dinitrophenylhydrazine.

3. The process of claim 2 wherein the Group A amine is selected from aniline, o-methylaniline, hydrazine, or hydrazine hydrate, and the Group B amine is m-phenylenediamine.

4. The process of claim 1 wherein the acrylic acid source feed stream is fed to the first distillation column at a temperature of from 40° to 80° C.

5. A continuous process for producing a pure grade acrylic acid (PGAA) comprising the steps of:

a) feeding to an acetic acid distillation column a feed stream at a temperature of from 25° to 100° C., the feed stream comprising:
   i) a high acetic acid-containing crude acrylic acid having greater than 2,000 ppm of acetic acid;
   ii) a minimum effective level in the range of from 0.1 to 2.0 molar ratio, based on total moles of aldehydes and maleic acid and maleic anhydride in the high acetic acid-containing crude acrylic acid, of at least one of a Group A amine selected from the group consisting of:

i) a primary arylamine of structure (I),

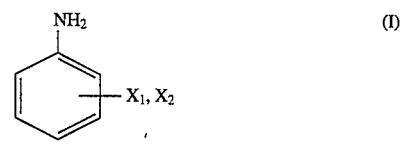

wherein $X_1$ and $X_2$ are selected from the group consisting of H, $NR_2$, OR, Cl, and R, wherein R is selected from H or $C_1$–$C_6$ alkyl;

ii) a hydrazine, optionally its hydrate, of structure $R^2$—NH—$NH_2$, wherein $R^2$ is selected from H, phenyl, 4-nitrophenyl, or 2,4-dinitrophenyl;

iii) an alkylenepolyamine of structure (II)

wherein $R^3$ is selected from H or a $C_1$–$C_6$ alkyleneamine, and $R^4$ is a $C_1$–$C_6$ alkyleneamine; and iv) an α-amino acid selected from the group consisting of structure III

wherein $R^5$ is selected from H, R, or $R^4$; arginine, aspartic acid, glutamic acid, histidine, and methionine;

b) distilling off acetic acid from the feed stream to provide a low acrolein crude acrylic acid having an acetic acid content less than 2,000 ppm and an acrolein content less than 10 ppm;

c) subsequently feeding to a final distillation column:
   i. the low acrolein crude acrylic acid, having acrolein content less than 10 ppm and acetic acid content less than 2,000 ppm, and
   ii. concurrently, to an upper portion of the final distillation column above the low acrolein crude acrylic acid feed, an amine feed stream comprising a minimum effective level of from 0.01 to 1.0 molar ratio, based on total moles of aldehydes and maleic acid and maleic anhydride in the low acrolein crude acrylic acid, of at least one of a Group B amine selected from the group consisting of o-, m-, p-phenylenediamine, 4-nitrophenyl-hydrazine, and 2,4-dinitrophenyl-hydrazine; and d) fractionally distilling the low acrolein crude acrylic acid through the final distillation column, distilling off PGAA having a residual individual aldehyde content less than 10 ppm.

6. The process of claim 5 wherein the Group A amine is selected from the group consisting of aniline, o-, m-, p-methylaniline, hydrazine, hydrazine hydrate, diethylenetriamine, glycine, lysine, and methionine, and the at least one of the Group B amine is selected from the group consisting of m-phenylenediamine, 4-nitrophenylhydrazine and 2,4-dinitrophenylhydrazine.

7. The process of claim 6 wherein the Group A amine is selected from aniline, o-methylaniline, hydrazine, or hydrazine hydrate, and the Group B amine is m-phenylenediamine.

8. The process of claim 5 wherein the feed stream is fed to the acetic acid distillation column at a temperature of from 40° to 80° C.

* * * * *